(12) United States Patent
Vainoras et al.

(10) Patent No.: US 9,662,028 B2
(45) Date of Patent: May 30, 2017

(54) METHOD AND SYSTEM FOR PREDICTING OF ACUTE HYPOTENSIVE EPISODES

(71) Applicant: Kaunas University of Technology, Kaunas (LT)

(72) Inventors: Alfonsas Vainoras, Kaunas (LT);
Zenonas Navickas, Kaunas (LT);
Mindaugas Balciunas, Vilnius (LT);
Arminas Ragauskas, Kaunas (LT);
Kristina Berskiene, Kaunas (LT);
Vytautas Petkus, Kaunas (LT);
Rimtautas Ruseckas, Kaunas (LT)

(73) Assignee: Kaunas University of Technology (LT)

( * ) Notice: Subject to any disclaimer, the term of this patent is extended or adjusted under 35 U.S.C. 154(b) by 0 days.

(21) Appl. No.: 14/754,010

(22) Filed: Jun. 29, 2015

(65) Prior Publication Data

US 2016/0374580 A1    Dec. 29, 2016

(51) Int. Cl.
| | |
|---|---|
| A61B 1/04 | (2006.01) |
| A61B 5/04 | (2006.01) |
| A61B 5/021 | (2006.01) |
| A61B 5/0402 | (2006.01) |
| A61B 5/00 | (2006.01) |
| A61B 5/0408 | (2006.01) |

(52) U.S. Cl.
CPC ......... *A61B 5/04012* (2013.01); *A61B 5/021* (2013.01); *A61B 5/0402* (2013.01); *A61B 5/04085* (2013.01); *A61B 5/7275* (2013.01); *A61B 5/746* (2013.01); *A61B 2505/03* (2013.01)

(58) Field of Classification Search
None
See application file for complete search history.

(56) References Cited

U.S. PATENT DOCUMENTS

| | | |
|---|---|---|
| 2014/0128758 A1 | 5/2014 | Galloway et al. |
| 2014/0323885 A1 | 10/2014 | Genc et al. |
| 2014/0364750 A1 | 12/2014 | Brumfield et al. |

(Continued)

OTHER PUBLICATIONS

Ghaffari, et al., "Parallel Processing of ECG and Blood Pressure Waveforms for Detection of Acute Hypotensive Episodes: A Simulation Study Using a Rish Scoring Model", Computer Methods in Biomechanics and Biomedical Engineering, vol. 13, No. 2, Apr. 2010, pp. 197-213.

(Continued)

*Primary Examiner* — Erica Lee
(74) *Attorney, Agent, or Firm* — St. Onge Steward Johnston and Reens, LLC

(57) ABSTRACT

A method and system of predicting a hypotensive episode in a patient using one or more time varying hypotension specific biomarkers corresponding to physiological processes in the patient. Data derived from sensors or other measurement devices such as ECG sensors can be used to generate biomarkers. The biomarkers can then be used to generate an acute hypotension prediction classifier, or monitored factor, derived from a three dimensional temporal representation of two or more biomarkers. When the monitored factor exceeds a predetermined threshold the method and system trigger an alarm before an appearance of a hypotensive episode in the patient.

14 Claims, 18 Drawing Sheets

(56) References Cited

U.S. PATENT DOCUMENTS

2015/0364022 A1* 12/2015 Dyell ............... A61B 5/162
340/573.1

OTHER PUBLICATIONS

Bikulciene, et al., "The Estimation of human Vital Signs Complexity", World Academy of Science, Engineering and Technology, International Journal of Medical, Health, Biomedical, Bioengineering and Pharmaceutical Engineering, vol. 8, No. 1. Jan. 1, 2014, pp. 39-44.
R. Donald, et al.; "Early Warning of EUSIG-Defined Hypotensive Events Using a Bayesian Artificial Neural Network"; M.U. Schuhmann and M. Czosnyka (eds.), Intracranial Pressure and Brain Monitoring XIV; Acta Neurochirurgica Supplementum vol. 114, DOI: 10. 107/978-3-7091-0956-4-8, Springer-Verlag/Wien 2012. pages 39-44.
A. Stell, et al.; "Federating distributed clinical data for the prediction of adverse hypotensive events" Philosophical Transactions of the Royal Society Publishing; Jun. 2009; <rsta.royalsocietypublishing.org> pp. 2678-2690.
R. Donald, et al.; "Trigger Characteristics of EUSIG-Defined Hypotensive Events" M.U. Schuhmann and M. Czosnyka (eds.), Intracranial Pressure and Brian Monitoring XIV, Acta Neurochirurgica Supplementum, vol. 114, DOI: 10.1007/978-3-7091-0956-4-9, Springer-Verlag/Wien 2012. pp. 45-49.

\* cited by examiner

Threshold (Area FIG3 step 4) =0.16
Time of predicting hypotensive event = 110 min Threshold (Dmax_Norm FIG3 , step5) =0.35
Time of predicting hypotensive event = 100 min Threshold ($r_{Dij}$ FIG3, step 7) =0.7
Time of predicting hypotensive event = 90 min Threshold ( FIG3, step 8) =0.2
Time of predicting hypotensive event = 93 min Threshold (FIG3, step 9) =0.28
Time of predicting hypotensive event = 98 min Threshold (FIG3, step 10) =0.7
Time of predicting hypotensive event = 88 min

METHOD AND SYSTEM FOR PREDICTING OF ACUTE HYPOTENSIVE EPISODES

FIELD OF THE INVENTION

A method and system of predicting a hypotensive episode using one or more time varying hypotensive biomarkers corresponding to physiological processes in the patient, and generating an acute hypotension prediction classifier based upon classification of 3D temporal representation of two or more biomarkers before an appearance of hypotensive episode.

BACKGROUND OF THE INVENTION

Acute hypotensive episodes (AHEs) are one of the most critical events that generally occur in intensive care units (ICUs). An acute hypotensive episode is a clinical condition typically characterized by abnormally low blood pressure values and other related values. For example, an acute hypotensive episode may occur in an interval of from 5 minutes up to 30 minutes or more during which at least 90% of the mean arterial pressure (MAP) measurements of a patient are at or below 70 mmHg. According to the other definition of acute hypotensive episode it appears when systolic value of arterial blood pressure (ABP) drops below 90 mmHg. Acute hypotensive episodes may occur due to a large number of causes. The causes of acute hypotensive episodes, among others, may include sepsis, myocardial infarction, cardiac arrhythmia, pulmonary embolism, hemorrhage, dehydration, anaphylaxis, medication, vasodilatory shock, or any of a wide variety of other causes. Often it may be crucial to determine the causes of the acute hypotensive episodes in order to administer appropriate patients' treatment before hypotensive episode. However, when the acute hypotensive episodes are not predicted in time, the practitioners are left with insufficient time to determine the causes of the acute hypotensive episodes and to start patient specific treatment. Also, due to insufficient time appropriate treatment may not be administered. If an acute hypotensive episode is not promptly and appropriately treated, it may result in an irreversible organ damage and, eventually death.

SUMMARY OF THE INVENTION

The method includes determining a plurality of time varying hypotensive biomarkers corresponding to plurality of physiological processes in patient's organism as a non-linear dynamic complex system and generating an acute hypotension prediction classifier. The acute hypotensive prediction classifier is based upon identifying and classifying a three dimensional (3D) temporal representation of two or more biomarker dynamics that appear before a hypotensive episode occurs.

Classification of the 3D temporal representation is based on calculation and comparison with the critical threshold of the mathematical index (root mean square (RMS) of 2D areas of 3D dynamic images under comparison, cross-correlation of 3D images, different Euclidian distances, etc.) representing time dependences of difference between 3D dynamic images. Such index versus time reflects temporal dynamics of the difference between an initial (or "Standard") 3D representation of selected high resolution ECG biomarkers (without or together with the additional biomarkers—oxygenation of microcirculatory blood flows monitored by NIRS, lung function estimated by monitoring of an end tidal CO2, etc.) and the evolution of such 3D representation in time before hypotensive episode.

An alarm signal, before the hypotensive event occurs, is generated when the mathematical index crosses the critical threshold. The alarm signal can be a visual alarm, audible alarm or both.

The system includes the high resolution (not less than 500 Hz) ECG subsystem. The additional monitors reflecting behaviour of the patient's organism as a holistic non-linear dynamic complex system before a hypotensive event can be included for example, near infrared spectroscopy (NIRS), end tidal expiratory CO2 concentration, etc. For example a personal computer (PC) is connected with the sensors and real-time monitors of plurality of biomarkers (selected ECG biomarkers, brain parenchymal blood oxygenation, end tidal expiratory CO2 concentration, etc.), processing subsystem that is configured to determine a plurality of selected time variation of selected biomarkers, acute hypotension episode prediction classifier's subsystem, which generates an alarm signal before hypotensive episode and which automatically makes alarm decision analyzing 3D temporal representation of two or more proposed biomarkers' comparing an initial "Standard" 3D representation and variable 3D representation before an appearance of hypotensive episode.

BRIEF DESCRIPTION OF THE DRAWINGS

These and other features and aspects of embodiments of the present invention will become better understood when the following detailed description is read with reference to the accompanying drawings in which like characters represent like parts throughout the drawings, wherein:

FIG. 5 illustrates normal or "Standard" 3D graph of selected biomarkers J(t) and V(t) long time (after 32 minutes from the start of ECG monitoring, FIG. 4) before hypotensive episode. The same time scale as in FIG. 4 is used in this figure and in FIG. 6-13. "Standard" here means 3D shape of two ECG biomarkers processed in the same way as illustrated in FIG. 2 and FIG. 3 in the case, when the patient with ECG monitoring has no hypotensive events within monitoring time from the start of monitoring.

DETAILED DESCRIPTION OF THE INVENTION

Figure 1:
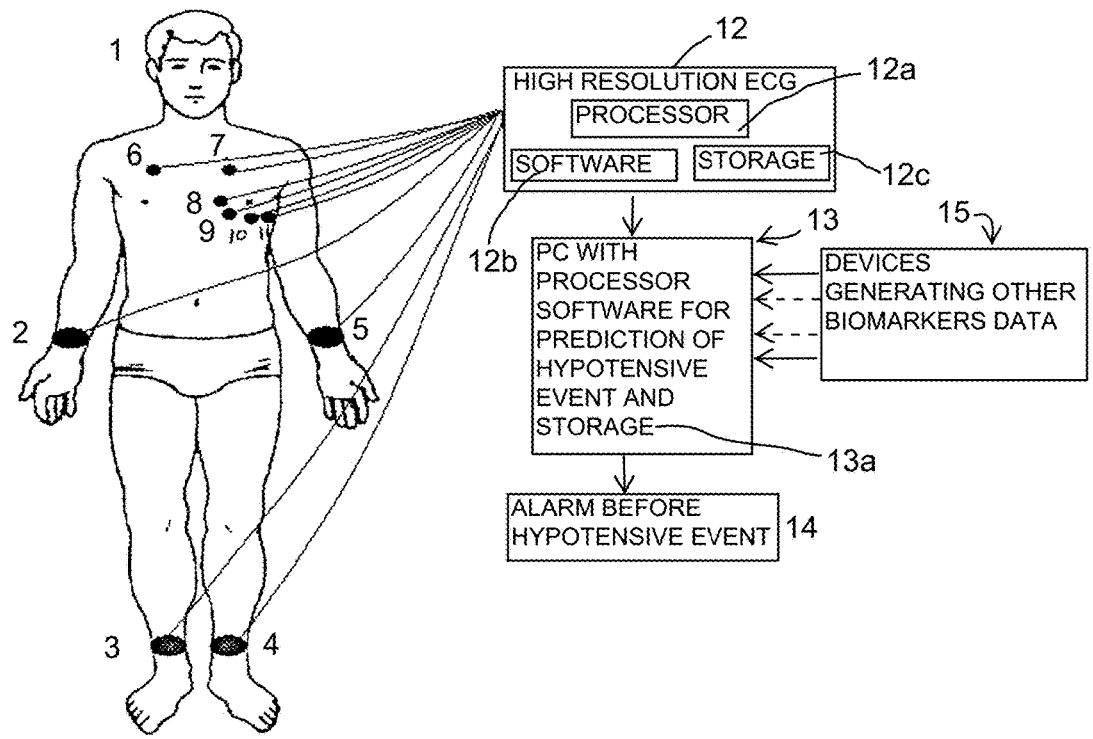
FIG. 1 is a block diagram of an acute hypotension prediction system, in accordance with one embodiment of the present invention.

Electrocardiography (ECG) is the process of recording the electrical activity of a patients heart over time using electrodes (sensors) placed on the patient's body. FIG. 1 is a general block diagram of one embodiment of the inventive system. FIG. 1 shows a patient (1) and 10 electrodes, or sensors (2-11) attached to the patient for transmitting ECG signals to the ECG device (12). The ECG device is preferably a high resolution ECG device having a processor (12a), software (12b) and storage (12c). The processor and software are capable of making calculations using data generated by measuring devices attached to patient that measure biological outputs such as processing and analyzing ECG or respiratory signals(15). The ECG device could also be connected to a personal computer (13) that includes a processor, software and storage (13a) capable of processing and analyzing the ECG signals in order to predict a hypotensive event. The system also includes storage (12a or 13a) for storing threshold alarm values that can be compared to processed data. The system also includes an alarm (14) which activates before a hypotensive event occurs and gives a warning signal to the caregivers when the system predicts an upcoming hypotensive event. The advance warning signal gives caregivers the opportunity to take corrective or remedial action with the patient before the hypotensive event occurs in order to avoid pathophysiological consequences and unfavorable outcome of patient after hypotensive event. The system also has the ability to receive other signals from other devices that generate data of physiological measurements that can be used to calculate hypotension prediction specific biomarkers. (15).

As will be described in detail hereinafter, systems and methods that predict potential acute hypotensive episodes in patients are presented. The systems and methods predict the potential acute hypotensive episodes in an automated manner without human interference. A rapid, accurate, sensitive and specific prediction of the potential acute hypotensive episodes may provide adequate time to diagnose the cause of the potential acute hypotensive episodes in the patients. Therefore, the prediction of the acute hypotensive episodes may improve possibilities of determination of the kind of intervention or treatment required to prevent the patients from the potential acute hypotensive episodes. In one embodiment, the systems and methods predict the potential acute hypotensive episodes in patients who are admitted in intensive care units (ICUs).

Figure 2:
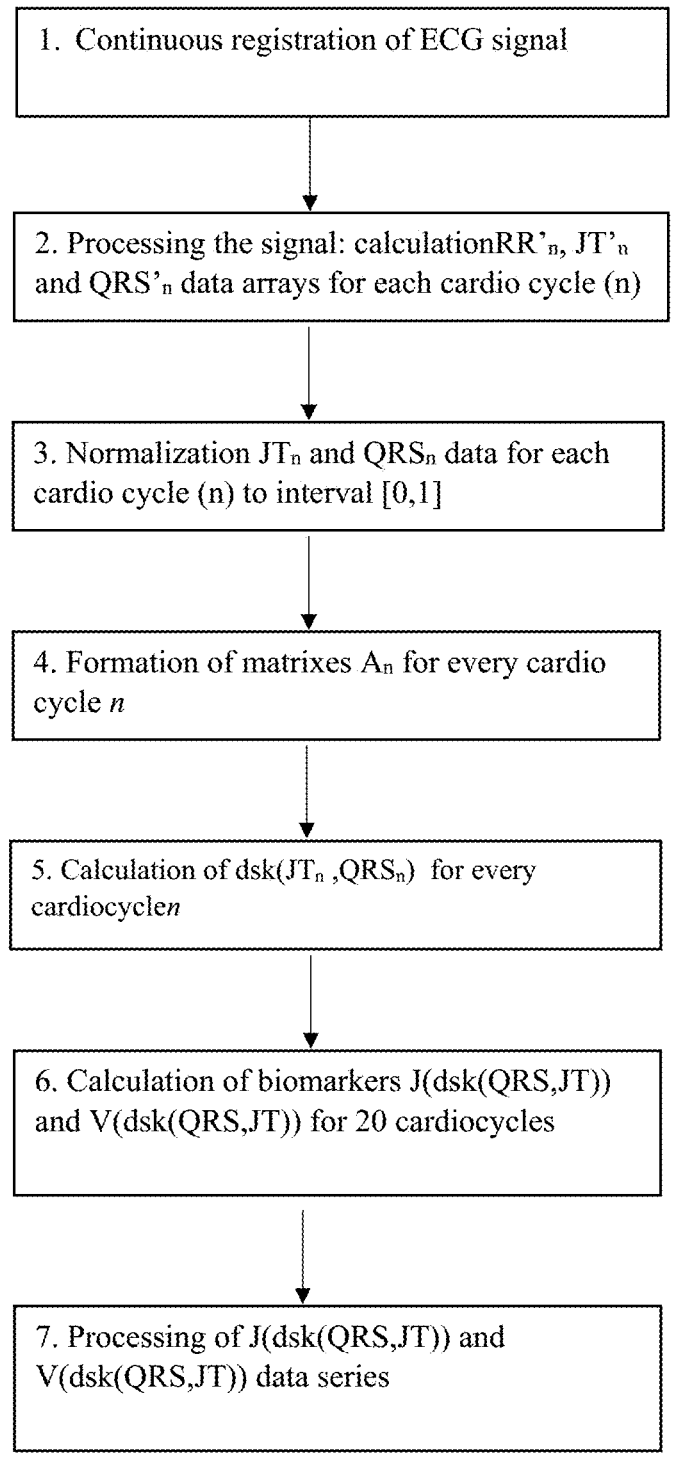
FIG. 2 and FIG. 3 are diagrammatic illustrations of the architecture of the ECG biomarkers' processing-subsystem referred to in FIG. 1, in accordance with one embodiment of the present invention.

Referring to FIG. 2, which is a diagrammatic illustration of the architecture of the ECG biomarkers processing—subsystem referred to in FIG. 1.

The processing of the ECG signal to derive the prognostic biomarkers V[dsk(JT,QRS)] and J[dsk(JT, QRS),JT] works as follows. ECG signals are received via sensors attached to a patient. The ECG signals from the sensors are preferably synchronous on a number of channels, preferably 10 to 12 channels, and the sampling frequency is not less than 500 Hz. This allows for continuous registration of the ECG signals with needed temporal resolution.

The ECG signal is processed for calculation of RR'n, JT'n and QRS'n intervals for use in data arrays for each cardio cycle (n) measured. For these calculations, $RR_n'$ is the duration of ECG RR interval meaning the time between 2 R peaks in milliseconds (ms). This interval is used as a time stamp (marker) for all calculations used during processing and also used for the synchronization of ECG and blood pressure data. $JT_n'$ is the duration of the ECG JT interval meaning the interval from the junction point J (at the end of the QRS interval) until the end of the T wave in ms. QRS'n is the duration of the ECG QRS complex interval in ms.

Normalization of the JTn and QRSn data for each cardio cycle (n) to interval [0,1] is also performed using the following formula:

$$JT = \frac{JT' - JT_{min}}{JT_{max} - JT_{min}}, \text{ where } JT_{min} = 140 \text{ ms}, JT_{max} = 40 \text{ ms}$$

QRS$_n$' is the duration interval of ECG QRS complex in ms. n=(0, 1, 2, etc.) is the number of cardio cycles measured.

$$QRS = \frac{QRS' - QRS_{min}}{QRS_{max} - QRS_{min}}, \text{ where } QRS_{min} = 40 \text{ ms}, QRS_{max} = 150 \text{ ms}$$

Processing then occurs for formation of matrixes An for every cardio cycle n. A series of second order matrixes is constructed as follows:

$$A_n := \begin{bmatrix} JT_n & JT_{n-1} - QRS_{n-1} \\ JT_{n+1} - QRS_{n+1} & QRS_n \end{bmatrix}$$

again, where n is the number of cardiocycles.

Calculation of dsk (JTn,QRSn) for every cardio cycle n is performed. Calculations of mathematical characteristics: difference of matrix $A_n$:dfr$A_n$:=$JT_n$−$QRS_n$, co-diagonal product of matrix $A_n$: cdp $A_n$:=($JT_{n-1}$−$QRS_{n-1}$)·($JT_{n+1}$−$QRS_{n+1}$). Discriminant is calculated as follows:

$$dsk(JT_n,QRS_n) = dsk\ A_n = (dfrA_n)^2 + 4cdp\ A_n.$$

Calculation of biomarkers J (dsk(JTn,QRSn)JT) and V (dsk(JTn,QRSn)) for 20 cardio cycles is performed as follows. The slope of linear dependence between dsk($JT_n$, $QRS_n$) and $JT_n$ for each 20 cardio cycles results in J(dsk (JT,QRS),JT); and the ratio between the standard deviation and the mean of dsk($JT_n$,$QRS_n$) in each 20 cardio cycles of dsk($JT_n$,$QRS_n$) results in V[dsk(JT,QRS)].

Figure 3:
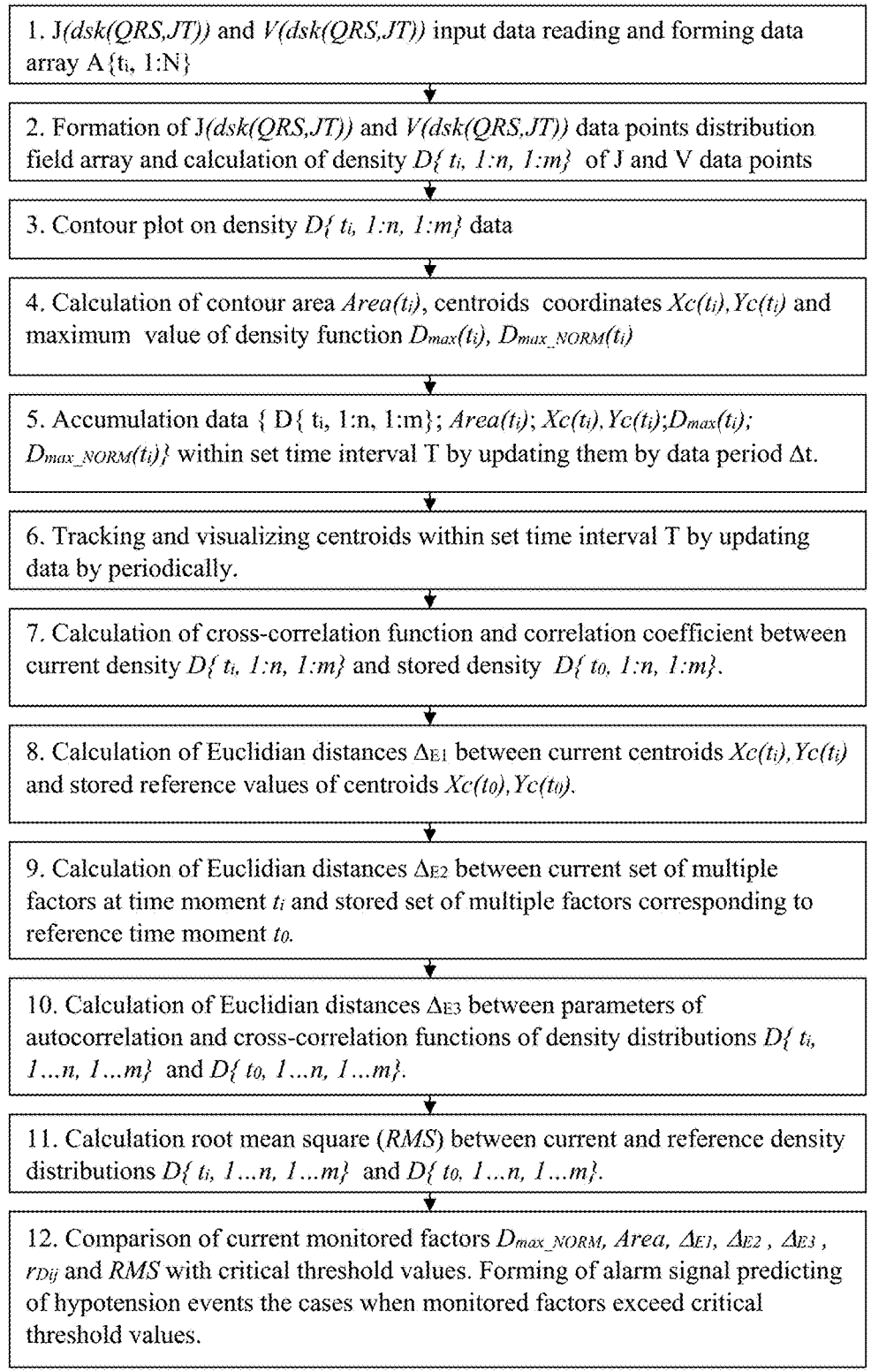
Figure 4:
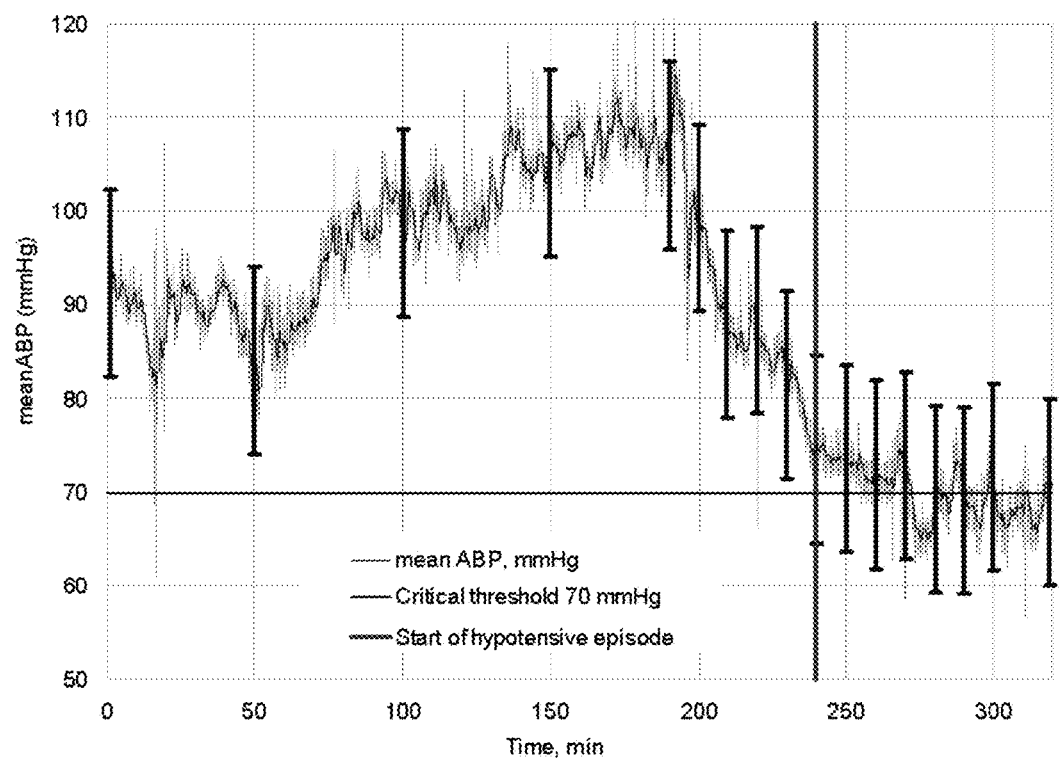
FIG. 4 is an exemplary graphical representation of invasively recorded mean arterial blood pressure (ABP) dynamics before and during hypotensive episode which is defined as a decrement of meanABP below 70 mmHg (or decrement of systolic ABP below 90 mmHg), in accordance with an embodiment of the present systems. Here the meanABP monitoring error bars show a typical uncertainty (+1-2 standard deviation (SD) of random errors, where SD=10 mmHg) corridor of real-time invasive ABP monitoring.
Figure 5:
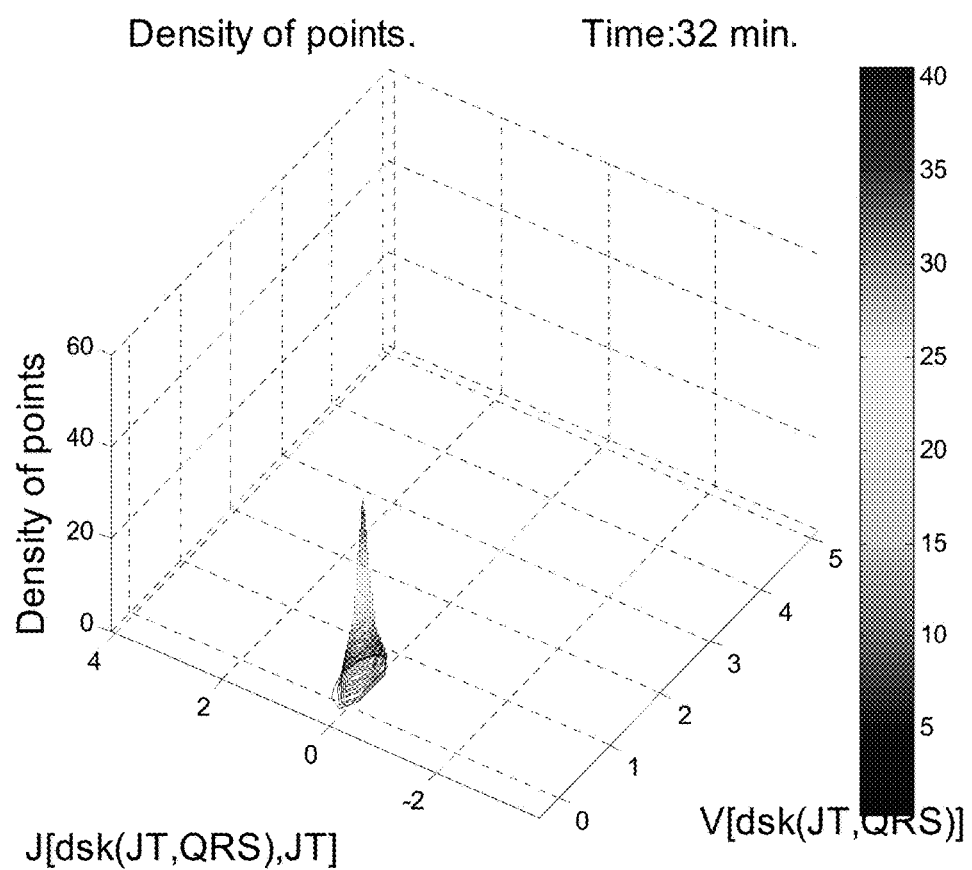
FIG. 5 is an exemplary 3D graphical representation or 3D image of two preprocessed selected ECG biomarkers: J(t) is the sensitivity of hypotension prediction specific biomarker and V(t)—hypotension prediction specific biomarker both of which are further explained and defined in the specification. J(t) and V(t) are calculated from monitoring data points' density within 5 minutes of monitoring time, in accordance with an embodiment of the present techniques.
Figure 6:
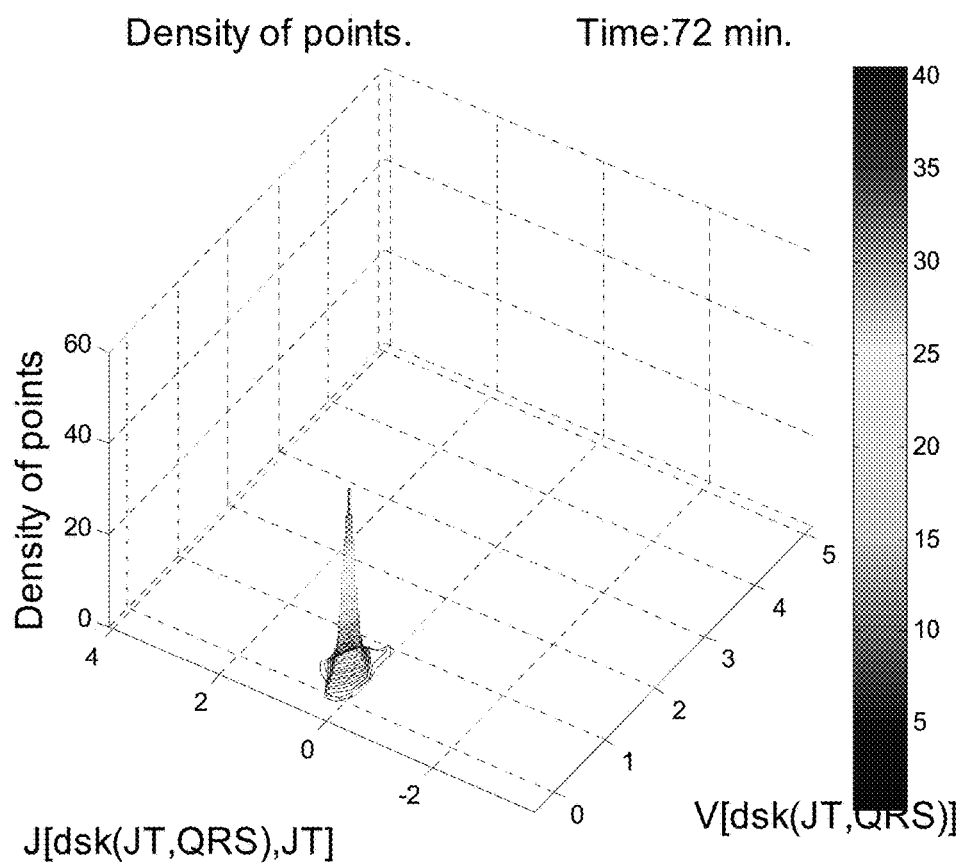
FIG. 6 is the same as FIG. 5, but at the time moment of 72 minutes from the start of ECG monitoring.
Figure 7:
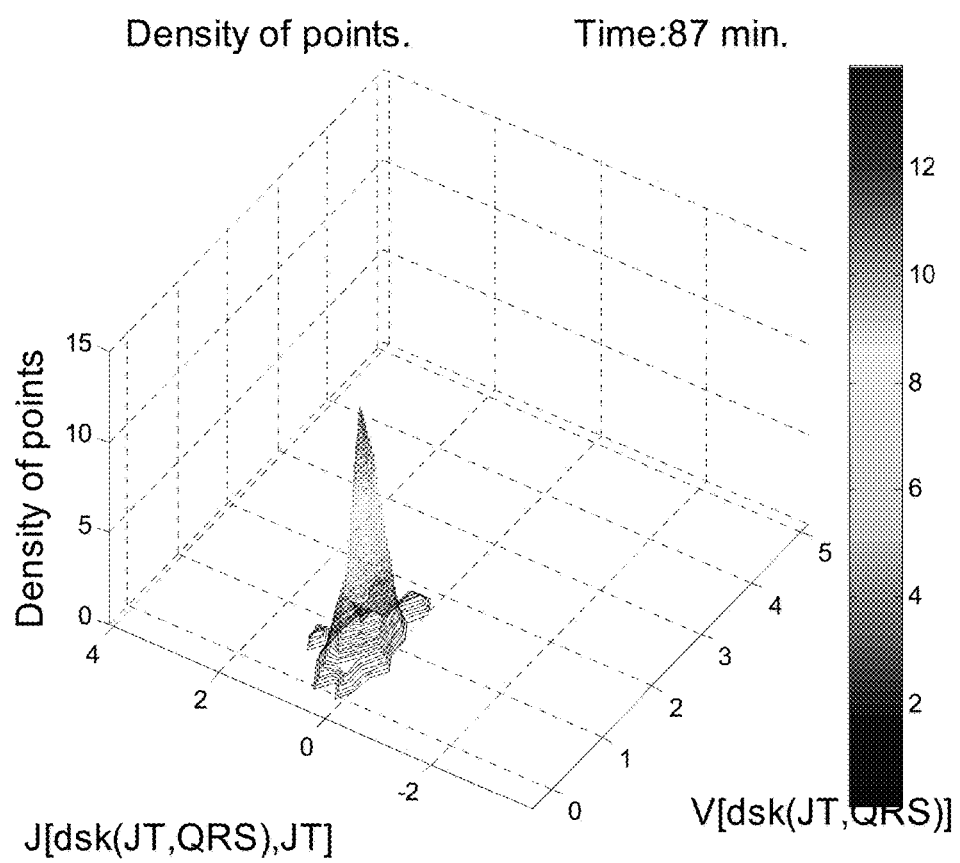
FIG. 7 is the same as FIG. 5, but at the time moment of 87 minutes from the start of ECG monitoring.
Figure 8:
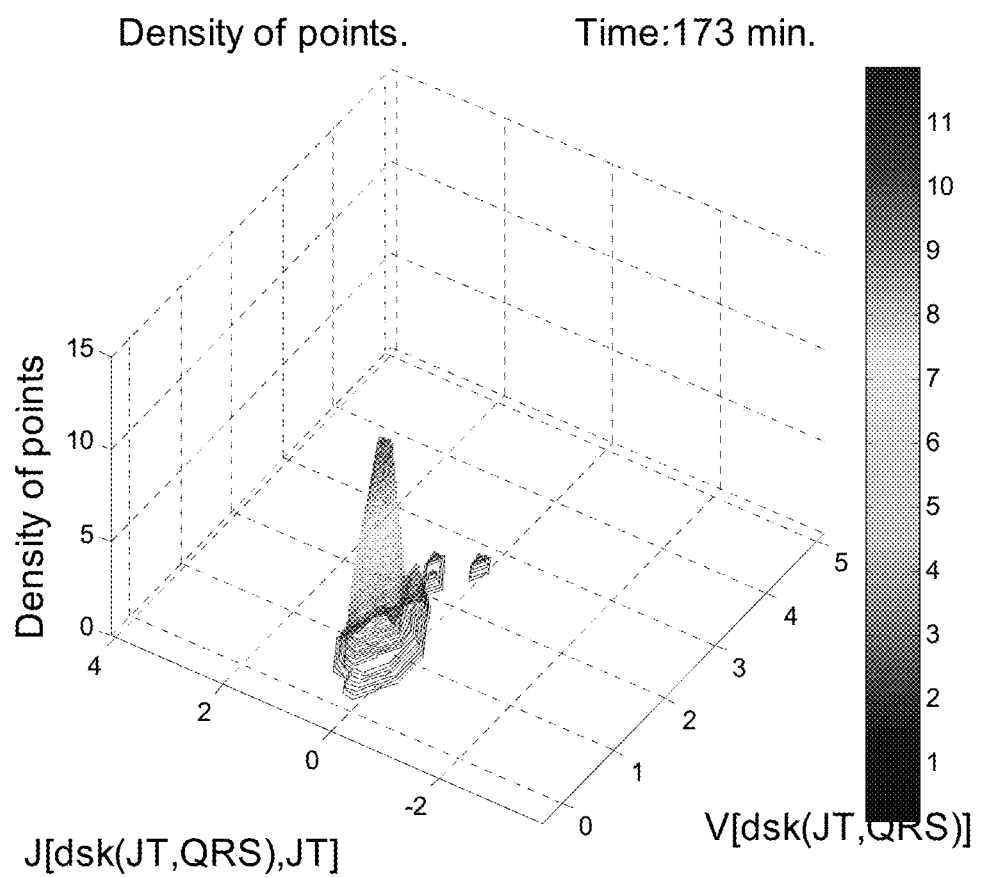
FIG. 8 is the same as FIG. 5, but at the time moment of 173 minutes from the start of ECG monitoring.
Figure 9:
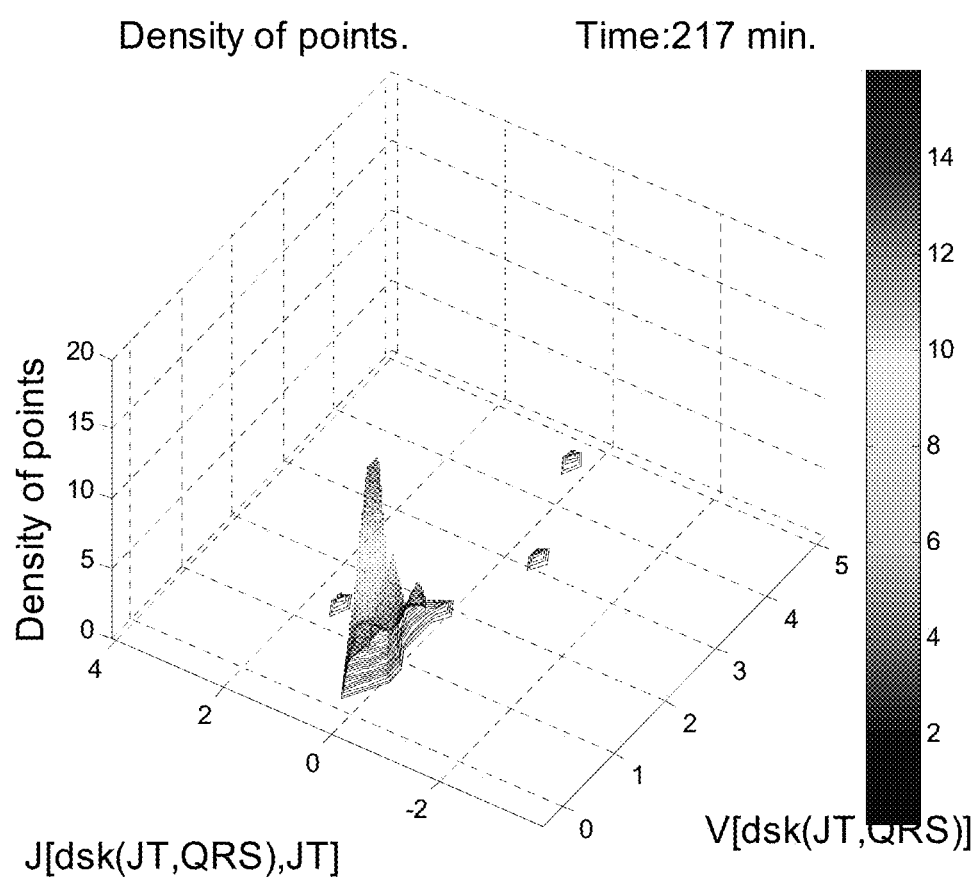
FIG. 9 is the same as FIG. 5, but at the time moment of 217 minutes from the start of ECG monitoring.
Figure 10:
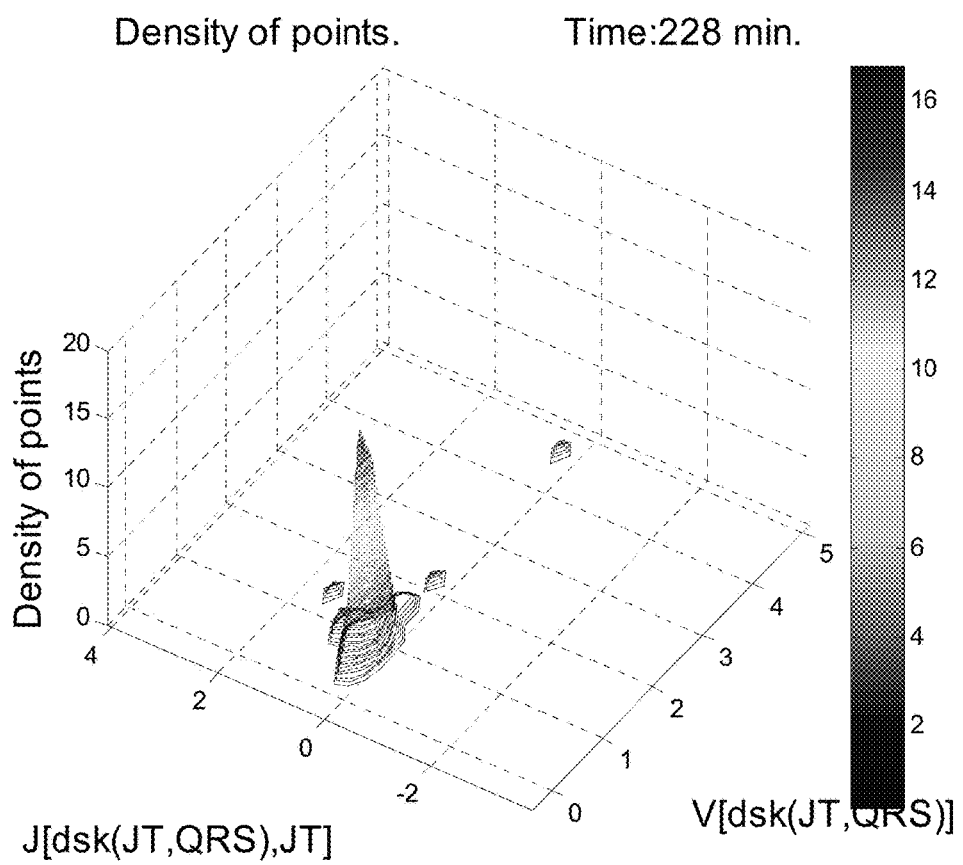
FIG. 10 is the same as FIG. 5, but at the time moment of 228 minutes from the start of ECG monitoring.
Figure 11:
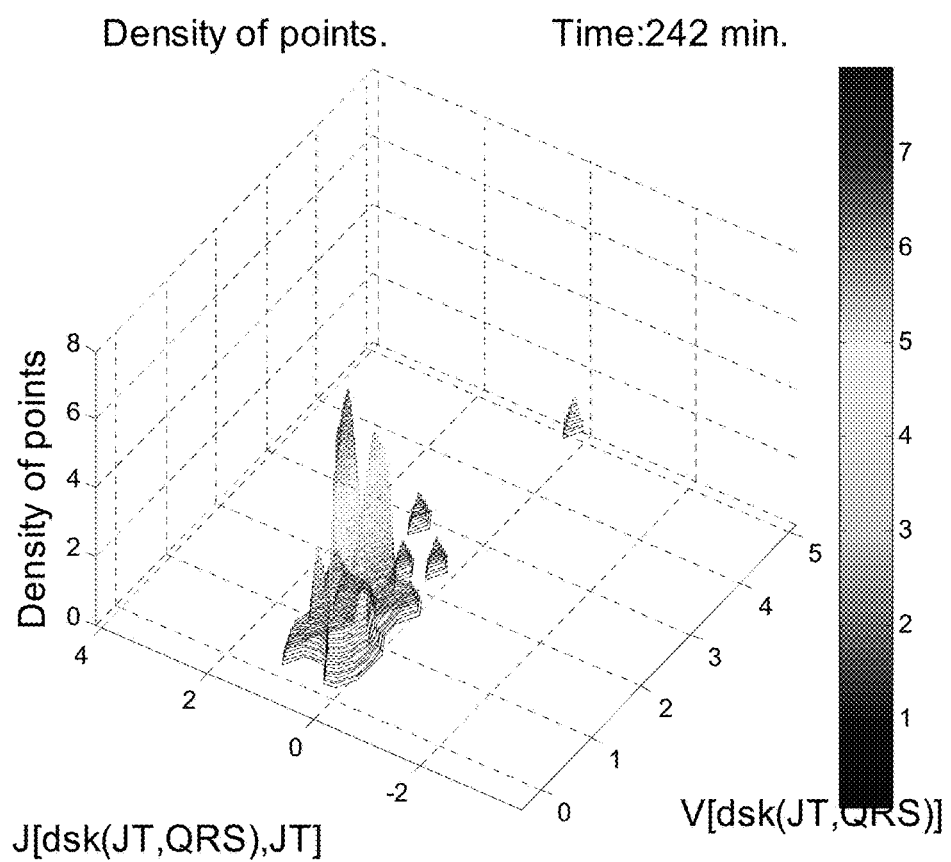
FIG. 11 is the same as FIG. 5, but at the time moment of 242 minutes from the start of ECG monitoring.
Figure 12:
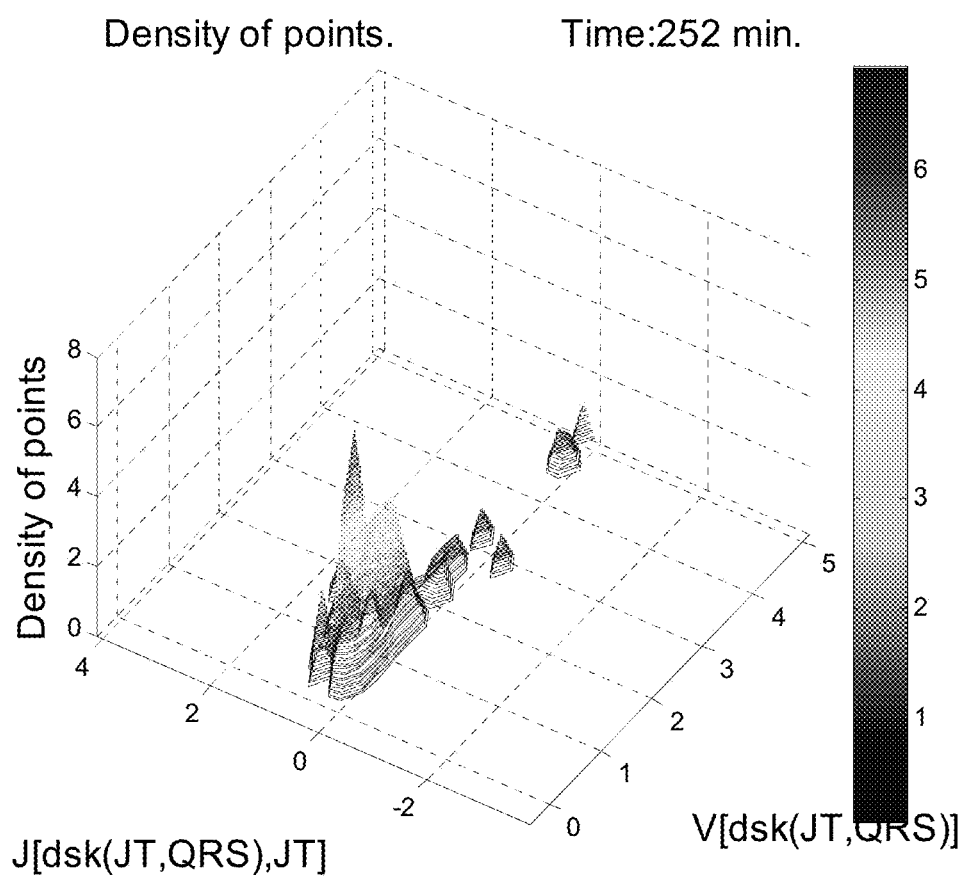
FIG. 12 is the same as FIG. 5, but at the time moment of 252 minutes from the start of ECG monitoring.
Figure 13:
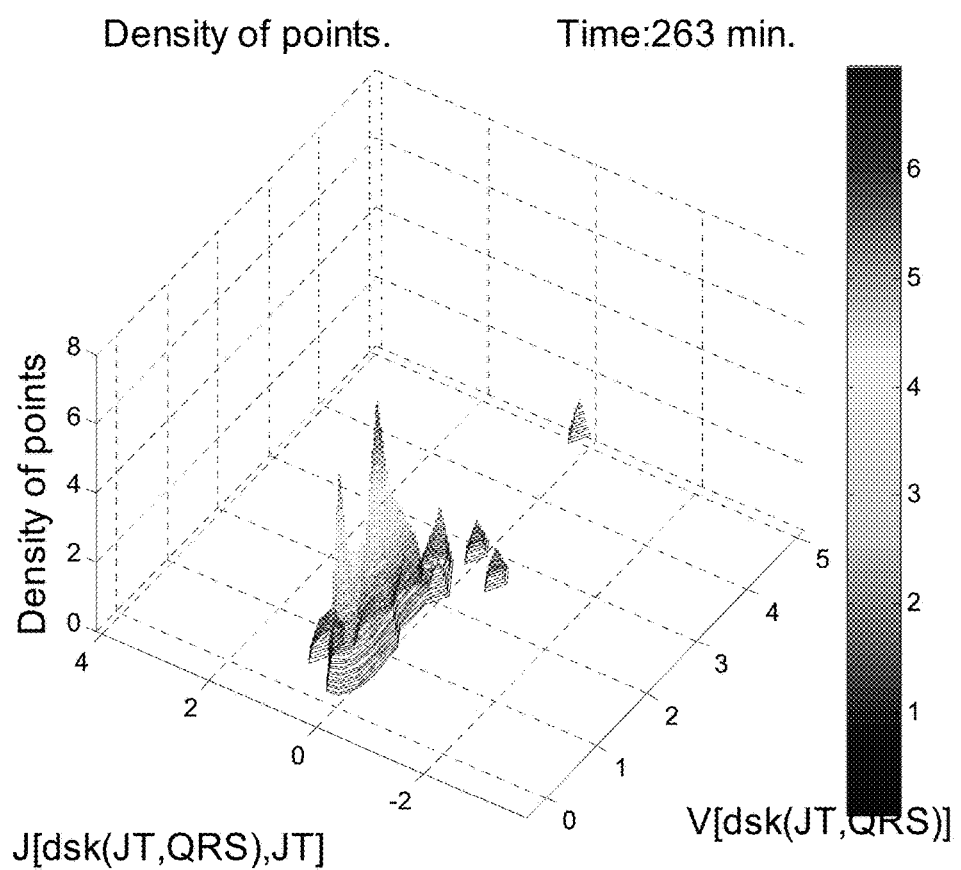
FIG. 13 is the same as FIG. 5, but at the time moment of 263 minutes from the start of ECG monitoring.

Processing of J(dsk(QRS,JT)JT) and V(dsk(QRS,JT)) data series is done in order to predict hypotensive events. One embodiment of the invention uses the following algorithm of J(dsk(QRS,JT)) and V(dsk(QRS,JT)) data processing for prediction of hypotension events as shown in FIG. 3. The preferred algorithm uses the following steps:

Input data of J(dsk(QRS,JT)) and V(dsk(QRS,JT)) pairs reading and forming of the data array A{$t_i$, 1 . . . N}. Data array A{$t_i$, 1 . . . N} is formed from pairs of J(dsk(QRS,JT) JT) and V(dsk(QRS,JT)) data points received within a set time interval (preferably 15 min). Approximate number of points of data array N is ~45 (~3 points per minute). Data are updated periodically every 5 minutes by forming new data array A{$t_i$, 1 . . . N}.

Formation of J(dsk(QRS,JT)) and V(dsk(QRS,JT)) data points distribution field array and calculation of density of J(dsk(QRS,JT)) and V(dsk(QRS,JT)) data points. Pairs of J(dsk(QRS,JT)JT) and V(dsk(QRS,JT)) points are plotted in field J(y—axis) vs V(x—axis). The field area is limited from min V=−0.5 to max V=5 in x axis. Field area is limited from min J=−4 to max J=4 in y axis. Limited area is segmented by steps $\Delta_v$=0.25 in x axis and $\Delta_s$=0.2 in y axis. Finally, the two dimensional (2D) array of data points distribution density—D{$t_i$, 1 . . . n, 1 . . . m} is calculated. (FIGS. 5-13). Here n is the number of discrete segments in x axis and m is the number of discrete segments in y axis.

Next, contour plot is calculated on density D{$t_i$, 1:n, 1:m} on set threshold level=0.29*max(D{$t_i$, 1 . . . n, 1 . . . m}). The contour plot also can be calculated from the density function D{$t_i$, 1:n, 1:m} using different threshold values, e.g. level+0.29 below the maximal value 1.0 of maxD or other levels.

Calculation of contour Area($t_i$), centroids coordinates Xc($t_i$) and Yc($t_i$) and maximum value of density function $D_{max}(t_i)$ and $D_{max\_NORM}(t_i)$. These parameters are calculated during each cycle of data processing:

Area of the contour is Area($t_i$). The sum value of all areas is calculated if there are only a few contours found. An example of graphing Area verses time can be seen in FIG. 15.

The coordinates of contour center of mass (centroids) Xc($t_i$) and Yc($t_i$). The centroids are calculated for the contour having maximal area, if there are only a few contours found.

Maximum value of density function $D_{max}(t_i)$=max (D{$t_i$, 1:n, 1:m}) and normalized value of maximum density $D_{max\_NORM}(t_i)$=max (D{$t_i$, 1:n, 1:m})/sum (D{$t_i$, 1:n, 1:m}).

Accumulating data within a set time interval T by updating them by data period $\Delta t$. Storing reference set of data {D{$t_0$, 1:n, 1:m}; Area($t_0$); Xc($t_0$),Yc($t_0$); $D_{max}(t_0)$; $D_{max\_NORM}(t_0)$} that corresponds the initial stable conditions. Tracking and visualizing centroids within set time interval T by updating data periodically also occurs. An example of graphing $D_{max\_NORM}$ verses time can be seen in FIG. 16.

Calculation of cross-correlation function and correlation coefficient between current density D{$t_i$, 1 . . . n, 1 . . . m} and stored density D{$t_0$, 1 . . . n, 1 . . . m} occurs. Calculation is performed of 2D cross-correlation function $c_{Dij}$ and 2D correlation coefficient $r_{Dij}$ between current D{$t_i$, 1 . . . n, 1 . . . m} and stored reference value of density distribution D{$t_0$, 1 . . . n, 1 . . . m}. Determination of peak coordinates $x_{peak\_C\_Dij}$ and $y_{peak\_C\_Dij}$ of cross-correlation function $c_{Dij}$. Calculation of 2D auto-correlation $c_{Dii}$ function for stored value of density distribution D{$t_0$, 1 . . . n, 1 . . . m}. Determination reference peak coordinates $x_{peak\_0}$ and $y_{peak\_0}$ of cross-correlation function $c_{Dii}$. An example of graphing $r_{Dij}$ verses time can be seen in FIG. 17.

Calculation of Euclidean distances $\Delta_{E1}$ between current centroids Xc($t_i$),Yc($t_i$) and stored reference centroid values Xc($t_0$),Yc($t_0$). An example of graphing $\Delta_{E1}$ verses time can be seen in FIG. 18.

Calculation of Euclidean distances $\Delta_{E2}$ between current set of multiple factors at time moment $t_i$ and stored set of reference multiple factors corresponding to time moment $t_0$. Set of multiple factors consists of:

centroids Xc($t_i$), Yc($t_i$)

Area($t_i$)

normalized maximum density $D_{max\_NORM}(t_i)$. An example of graphing $\Delta_{E2}$ verses time can be seen in FIG. 19.

Calculation of Euclidean distances $\Delta_{E3}$ between parameters of autocorrelation and cross-correlation functions of density distributions current density D{$t_i$, 1 . . . n, 1 . . . m} and stored density D{$t_0$, 1 . . . n, 1 . . . m}. Calculation of Euclidean distances $\Delta_{E3}$ of peak coordinates shift $x_{peak\_C\_Dij}$ and $y_{peak\_C\_Dij}$ from reference peak coordinates $x_{peak\_0}$ and $y_{peak\_0}$. An example of graphing $\Delta_{E3}$ verses time can be seen in FIG. 21.

Calculation root mean square (RMS) between current density distribution D{$t_i$, 1 . . . n, 1 . . . m} and stored reference value of density distribution D{$t_0$, 1 . . . n, 1 . . . m}. An example of graphing RMS can be seen in FIG. 14.

Figure 14:
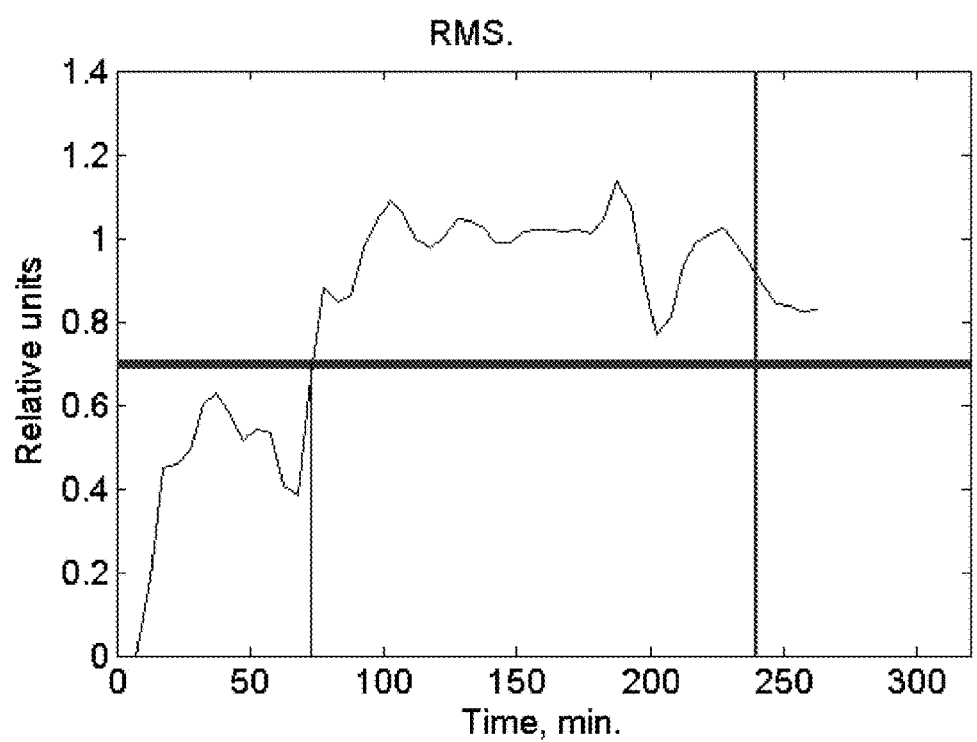
FIG. 14 is a diagrammatic illustration of root mean square, verses time, RMS(t) function calculated comparing initial or "Standard" 3D image (FIG. 5) with other monitored 3D images (some of them are presented in FIGS. 6-13) before the start of the hypotensive episode at approximately 240 seconds (when meanABP crosses the critical threshold presented in FIG. 4) in accordance with one embodiment of the present system.

Compare current values of monitored factors $D_{max\_NORM}$, Area, $\Delta_{E1}$, $\Delta_{E2}$, $\Delta_{E3}$, $r_{Dij}$ or RMS versus time with critical threshold values, or alarm values. Forming of alarm signal predicting of the hypotension episode the cases when monitored factors meets, reaches or exceeds the critical threshold values or alarm values. For example, FIG. 14 shows a graph of RMS calculations in relative units verses time and the RMS(t) crossing the critical threshold of 0.7 at a time approximately 75 minutes on the x-axis.

Figure 15:
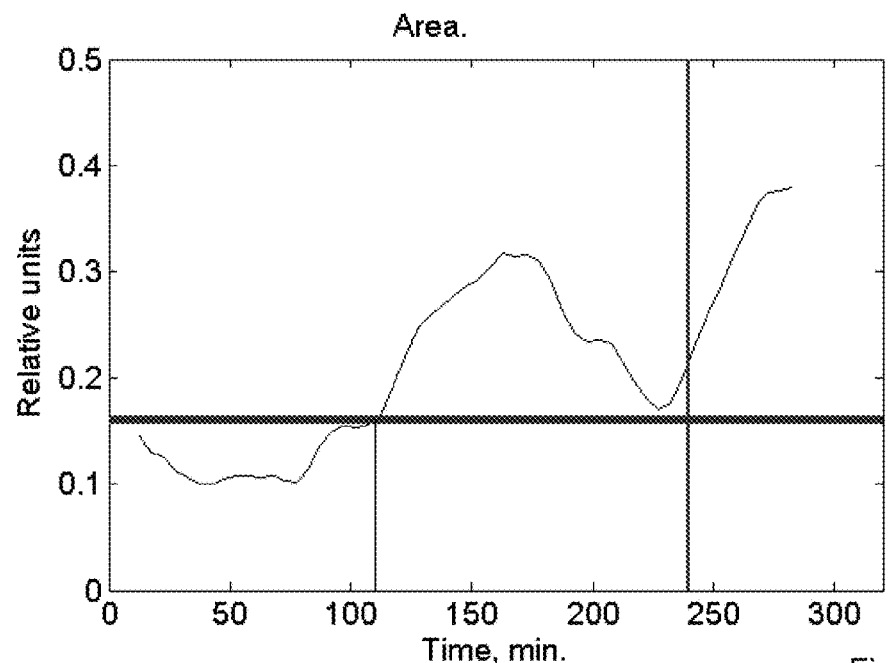
FIG. 15 is a diagrammatic illustration of an Area verses time calculated comparing initial or "Standard" 3D image (FIG. 5) with other monitored 3D images (some of them are presented in FIGS. 6-13) before the start of the hypotensive episode at approximately 240 seconds in accordance with one embodiment of the present system.

FIG. 15 shows a graph of Area in relative units verses time with the threshold number equal to 0.16 relative units. The graph shows the time of predicting the hypotensive event is at approximately 110 minutes as that is the time the measured units value reaches the threshold number. At this time, because the measured factor reaches the threshold value the processor can be programmed to generate an alarm to warn of the predicted upcoming hypotensive event.

Figure 16:
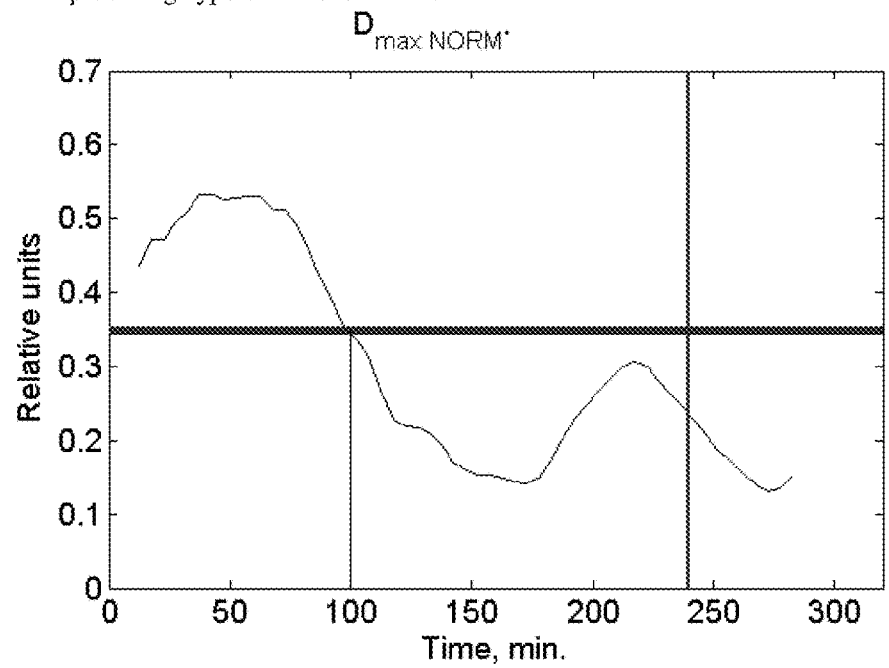
FIG. 16 is a diagrammatic illustration of a $D_{max\_NORM}$ verses time calculated comparing initial or "Standard" 3D image (FIG. 5) with other monitored 3D images (some of them are presented in FIGS. 6-13) before the start of the hypotensive episode at approximately 240 seconds in accordance with one embodiment of the present system.

FIG. 16 shows a graph of $D_{max\_NORM}$ in relative units verses time with the threshold number equal to 0.35 relative units. The graph shows the time of predicting the hypotensive event is at approximately 110 minutes as that is the time the measured units reaches the threshold number. At this time, because the measured factor reaches the threshold value the processor can be programmed to generate an alarm to warn of the predicted upcoming hypotensive event.

Figure 17:
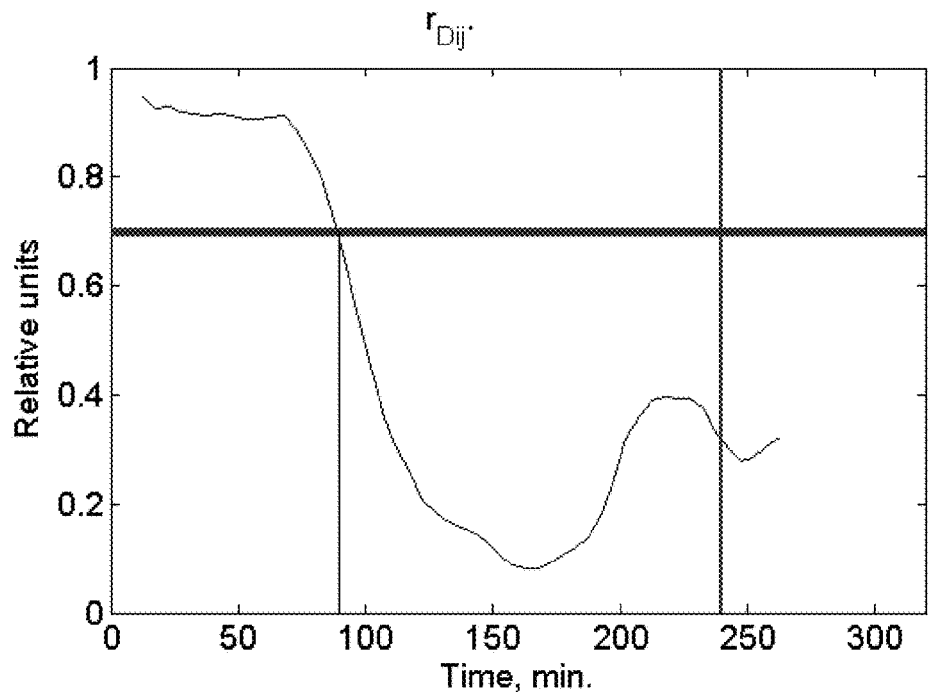
FIG. 17 is a diagrammatic illustration of $r_{Dij}$ verses time calculated comparing initial or "Standard" 3D image (FIG. 5) with other monitored 3D images (some of them are presented in FIGS. 6-13) before the start of the hypotensive episode at approximately 240 seconds in accordance with one embodiment of the present system.

FIG. 17 shows a graph of $r_{Dij}$ in relative units verses time with the threshold number equal to 0.7 relative units. The graph shows the time of predicting the hypotensive event is at approximately 90 minutes as that is the time the measured units reaches the threshold number. At this time, because the measured factor reaches the threshold value the processor can be programmed to generate an alarm to warn of the predicted upcoming hypotensive event.

Figure 18:
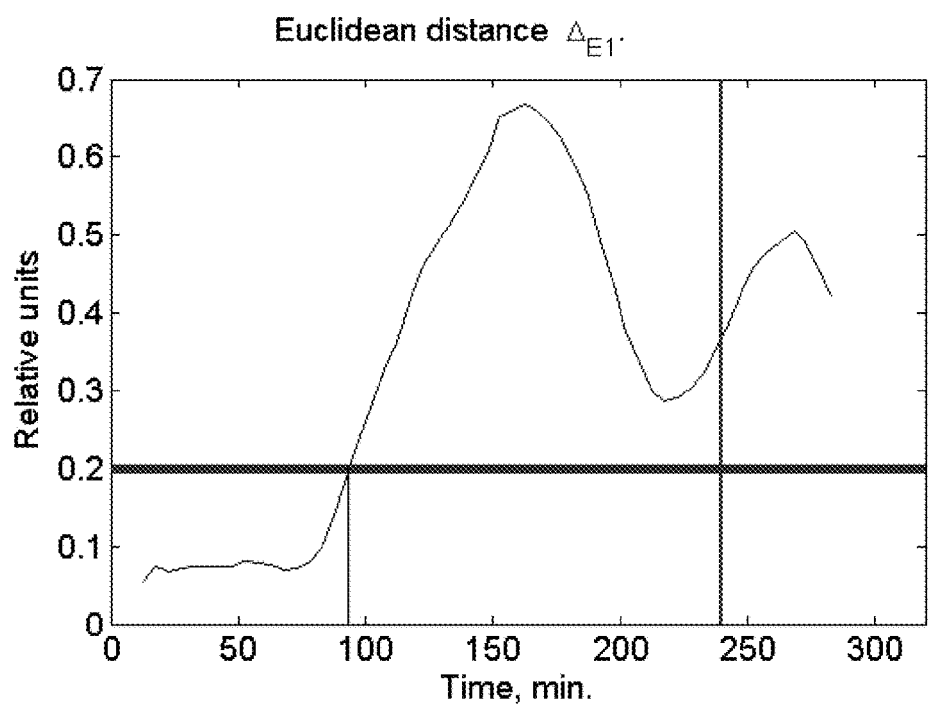
FIG. 18 is a diagrammatic illustration of $\Delta_{E1}$ verses time comparing initial or "Standard" 3D image (FIG. 5) with other monitored 3D images (some of them are presented in FIGS. 6-13) before the start of the hypotensive episode at approximately 240 seconds in accordance with one embodiment of the present system.

FIG. 18 shows a graph of $\Delta_{E1}$ in relative units verses time with the threshold number equal to 0.2 relative units. The graph shows the time of predicting the hypotensive event is at approximately 93 minutes as that is the time the measured units reaches the threshold number. At this time, because the measured factor reaches the threshold value the processor can be programmed to generate an alarm to warn of the predicted upcoming hypotensive event.

Figure 19:
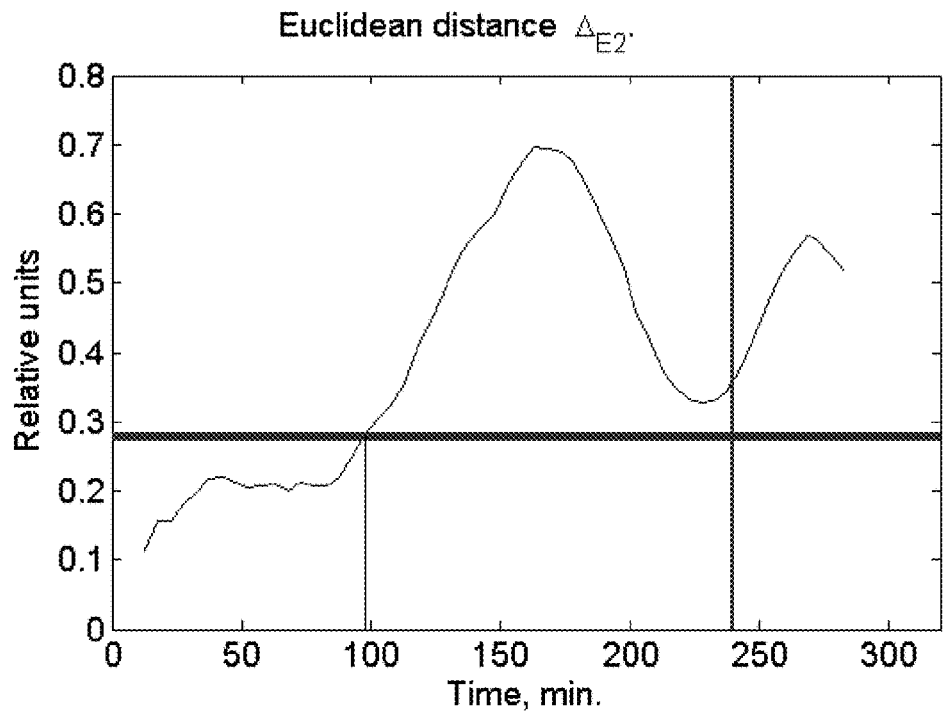
FIG. 19 is a diagrammatic illustration of a $\Delta_{E2}$ verses time, calculated comparing initial or "Standard" 3D image (FIG. 5) with other monitored 3D images (some of them are presented in FIGS. 6-13) before the start of the hypotensive episode at approximately 240 seconds in accordance with one embodiment of the present system.

FIG. 19 shows a graph of $\Delta_{E2}$ in relative units verses time with the threshold number equal to 0.28 relative units. The graph shows the time of predicting the hypotensive event is at approximately 98 minutes as that is the time the measured units reaches the threshold number. At this time, because the measured factor reaches the threshold value the processor can be programmed to generate an alarm to warn of the predicted upcoming hypotensive event.

Figure 20:
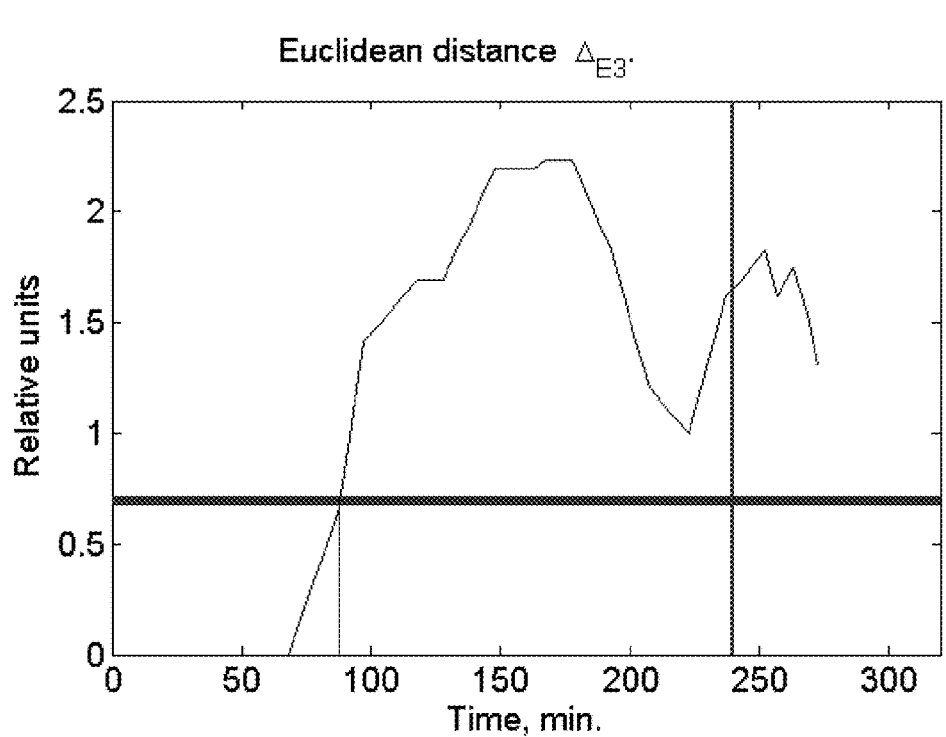
FIG. 20 is a diagrammatic illustration of a $\Delta_{E3}$ verses time calculated comparing initial or "Standard" 3D image (FIG. 5) with other monitored 3D images (some of them are presented in FIGS. 6-13) before the start of the hypotensive episode at approximately 240 seconds in accordance with one embodiment of the present system.

FIG. 20 shows a graph of $\Delta_{E3}$ in relative units verses time with the threshold number equal to 0.7 relative units. The graph shows the time of predicting the hypotensive event is at approximately 88 minutes as that is the time the measured units reaches the threshold number. At this time, because the measured factor reaches the threshold value the processor can be programmed to generate an alarm to warn of the predicted upcoming hypotensive event.

The invention contemplates one or more or various combinations of the monitored factors being used to determine when an alarm should be generated to warn of an upcoming hypotensive event. While single monitored factors can be used to trigger and alarm the sensitivity of different monitored factors can vary in clinical testing. Accordingly, other embodiments use a combination of more than one monitoring factor in an integrated alarm. The integrated alarm can be set to trigger in a variety of circumstances. For example, it can be triggered when more than one monitoring factors shows an alarm or it can be triggered when a majority of the monitored factors being monitored it triggered indicating and showing an alarm. In the preferred embodiment, all monitored factors are used to decide if an alarm should be triggered when a majority of the monitored factors cross their thresholds.

Affirmative prediction is indicated by comparing two 3D images—initial one peak image and other images with less height than the main peak and with other peaks which represent chaotic process. The 3D image representing the chaotic process reflects the patient's organism is approaching hypotensive event. When the patient is healthy the system measurements will generate images which will show a simple peak representative of a steady state. As the patient becomes less healthy, begins to depart from a steady state the system measurements will generate more chaotic images. The closer the patient gets to a hypertensive event the more and more chaotic the images become (as the system measurements move further from a steady state) which is indicative of a system when the organism as a non-linear complex dynamic system is unstable.

Euclidian distance can be one of the possible ways to monitor the difference between the initial 3D image of proposed biomarker and the next time generated images as the time gets closer to a hypotensive event. Correlation is another way to monitor such differences. Other image analysis methods can also be used, like RMS(t) function.

Figure 21:
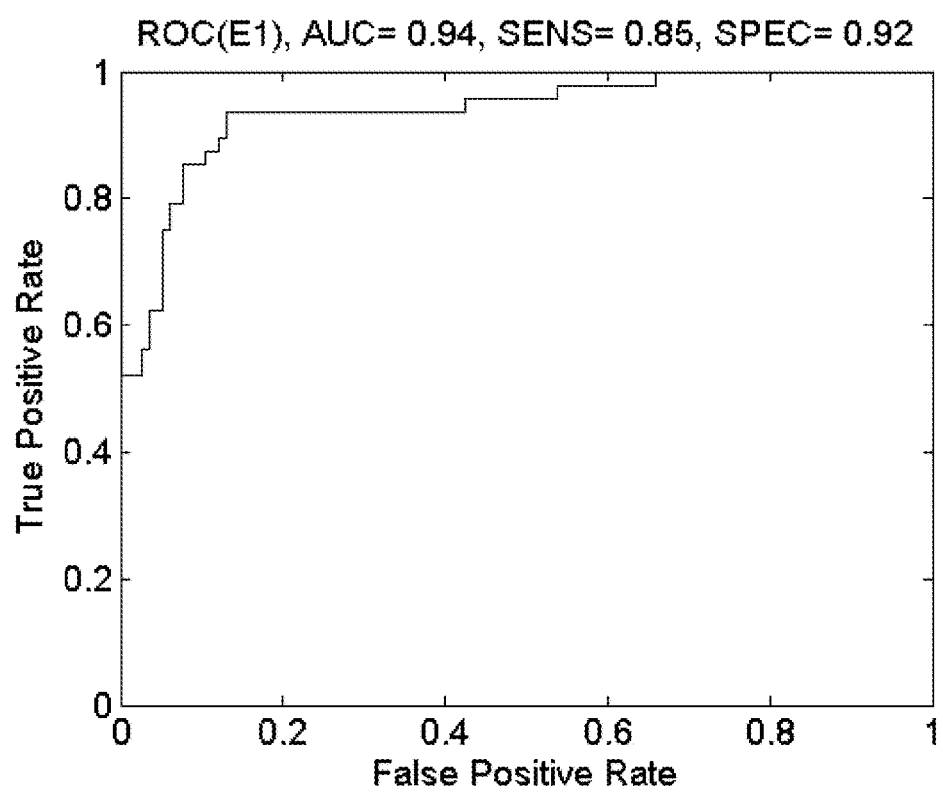
FIG. 21 is a Receiver Operation Characteristic (ROC) curve generated from cardiologic patients validating and confirming the reliability of the invention method and device.

FIG. 21 is a Receiver Operation Characteristic (ROC) curve generated from cardiologic patients validating and confirming the reliability of the invention method and device. The inventive method and system (FIG. 1) has been prospectively validated on 60 patients of cardiological intensive care units of three independent cardiological clinics. Patients with and without hypotensive episodes were included into prospective clinical study. ROC analysis has been used for estimation of sensitivity, specificity and area under curve (AUC) of hypotension episode prediction system. FIG. 21 shows the ROC curve of the clinically validated system using the most reliable monitoring factor $\Delta_{E1}$. The ROC curve confirms that the inventive hypotension episode prediction method and apparatus predicthypotensive episodes with very high and clinically acceptable sensitivity at 85% and specificity at 92%. The Area Under the ROC Curve (AUC) is also high at 94%. Sensitivity, specificity and AUC values all confirm that invented system solves the problem of reliable prediction of hypotensive episodes and that it can be widely used in clinical practice Although the invention has been described with reference to a particular arrangement of parts, features and the like, these are not intended to exhaust all possible arrangements or features, and indeed many other modifications and variations will be ascertainable to those of skill in the art.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A method for predicting an acute hypotensive episode of a patient comprising:
attaching electrocardiography sensors to a patient;
transmitting electrocardiography signals generated by the sensors attached to the patient, over a number of cardio cycles, to an electrocardiography device comprising a processor, software, storage, and a threshold alarm value stored in said storage;

processing the electrocardiography signals using the processor to calculate data for each cardio cycle;

forming matrixes for each cardio cycle using the calculated data;

calculating biomarkers using calculated data, wherein the biomarkers comprise biomarkers J(dsk(QRS,JT)JT) and V(dsk(QRS,JT));

generating a monitored factor using said biomarkers;

comparing said monitored factor to a threshold alarm value for said monitored value;

triggering an alarm when said threshold alarm value is exceeded by said monitored factor.

2. The method of claim 1 wherein said biomarkers are graphed in three dimensions to create three dimensional plots.

3. The method of claim 2 wherein the monitored factors comprising normalized value of maximum density (Dmax_NORM), contour area, Euclidean distance between centroids ΔE1, Euclidean distance between centroids and area ΔE2, Euclidean distance between parameters of autocorrelation and cross correlation functions of density E3, correlation coefficient (rDij) and root mean square (RMS) of the three dimensional plots versus time are generated based on the three dimensional plots.

4. The method of claim 2 wherein said biomarkers further comprise biomarkers for brain parenchymal blood oxygenation and biomarkers for end tidal expiratory carbon dioxide ($CO_2$) concentration.

5. The method of claim 1 wherein said monitored factor is one of normalized value of maximum density (Dmax_NORM), contour area, Euclidean distance between centroids ΔE1, Euclidean distance between centroids and area ΔE2, Euclidean distance between parameters of autocorrelation and cross correlation functions of density ΔE3, correlation coefficient (rDij) or root mean square (RMS).

6. The method of claim 5 wherein said monitored factor is root mean square (RMS) versus time.

7. The method of claim 5 wherein said monitored factor is Euclidean distance between centroids ΔE1.

8. The method of claim 1 wherein in a second monitored factor is generated using said biomarkers comparing said second monitored factor to a second alarm threshold and triggering said alarm when said first and said second threshold alarms are exceeded by said first and said second monitored factors.

9. A system for predicting an acute hypotensive episode of a patient comprising:

electrocardiography sensors for attaching to a patient;

leads coupled to said electrocardiography sensors for transmitting electrocardiography signals generated by the sensors attached to the patient, and also coupled to an electrocardiography device comprising a processor, software executing on said processor, and storage coupled to and accessible to said processor storing a threshold value;

said processor and software receiving the electrocardiography signals and calculating data for each cardio cycle;

said processor and software forms matrixes for each cardio cycle using the calculated data;

said processor and software calculates biomarkers using said calculated data wherein the biomarkers comprise biomarkers J(dsk(QRS,JT)JT) and V(dsk(QRS,JT)) and biomarkers for brain parenchymal blood oxygenation and biomarkers for end tidal expiratory carbon dioxide ($CO_2$) concentration;

said processor and software generates a monitored factor using said biomarkers;

said processor and software compares said monitored factor to the threshold value stored in said storage;

said processor and software generates an alarm when said monitored factor reaches said threshold.

10. The system of claim 9 wherein said biomarkers are processed by said processor and software and are graphed in three dimensions to create three dimensional plots.

11. The system of claim 10 wherein the processer and software generates on a three dimensional plots the monitored factors comprising normalized value of maximum density (Dmax_NORM), contour area, Euclidean distance between centroids ΔE1, Euclidean distance between centroids and area ΔE2, Euclidean distance ΔE3 between parameters of autocorrelation and cross correlation functions of density, correlation coefficient (rDij) and root mean square (RMS) of the three dimensional plots versus time.

12. The system of claim 9 wherein said processor and software generates a monitored factor, at least one of which is normalized value of maximum density (Dmax_NORM), contour area, Euclidean distance between centroids ΔE1, Euclidean distance between centroids and area ΔE2, Euclidean distance between parameters of autocorrelation and cross correlation functions of density ΔE3, correlation coefficient (rDij) or root mean square (RMS) versus time.

13. The system of claim 9 wherein said monitored factor is Euclidean distance between centroids ΔE1.

14. The system of claim 9 wherein said processor and software generates a second monitored factor using said biomarkers and said processor and software, compares said second monitored factor to a second alarm threshold, said processor and software triggering said alarm when said first and said second threshold alarm s are exceeded by said first and said second monitored factors.

* * * * *